United States Patent [19]

Haskell et al.

[11] 4,054,613
[45] Oct. 18, 1977

[54] BUTADIENE PRODUCTION AND PURIFICATION

[75] Inventors: Donald M. Haskell; Edward E. Hopper; Bradley L. Munro, all of Bartlesville, Okla.

[73] Assignee: Phillips Petroleum Company, Bartlesville, Okla.

[21] Appl. No.: 624,096

[22] Filed: Oct. 20, 1975

[51] Int. Cl.² .............................................. C07C 11/12
[52] U.S. Cl. .......................... 260/680 R; 260/677 A; 260/681.5 R; 203/57; 203/58; 203/62
[58] Field of Search ................... 203/50, 57, 58, 63, 203/70, 62; 260/681.5 R, 678, 677 A, 680 R, 680 E

[56] References Cited

U.S. PATENT DOCUMENTS

| | | | |
|---|---|---|---|
| 2,360,859 | 10/1944 | Evans et al. | 208/240 |
| 2,360,861 | 10/1944 | Pierotti et al. | 208/240 |
| 2,455,803 | 12/1948 | Pierotti | 203/51 |
| 2,849,514 | 8/1958 | Nevitt | 203/63 |
| 3,000,794 | 9/1961 | Tschopp | 260/681.5 R |
| 3,026,253 | 3/1962 | Woerner | 260/681.5 R |
| 3,059,037 | 10/1962 | Cahn | 203/54 |
| 3,230,157 | 1/1966 | Hill et al. | 203/53 |
| 3,242,227 | 3/1966 | Kroeper | 260/681.5 |
| 3,317,627 | 5/1967 | King et al. | 260/681.5 R |
| 3,436,438 | 4/1969 | Takao et al. | 260/681.5 R |
| 3,864,279 | 2/1975 | Pitzer | 260/680 E |
| 3,925,499 | 12/1975 | Pitzer | 260/680 E |
| 3,943,068 | 3/1976 | Ripley | 260/680 E |

*Primary Examiner*—O. R. Vertiz
*Assistant Examiner*—Eugene T. Wheelock

[57] ABSTRACT

Butadiene is produced in relatively pure form by an oxidative dehydrogenation process in which a crude butadiene stream comprising butadiene, butylenes, vinyl acetylene and propylene is first extractively distilled with an extractant consisting of a sulfolane/acetone mixture. From a purified stream consisting essentially of butadiene and vinyl acetylene, the vinyl acetylene in a second extractive distillation step is removed using a sulfolane/acetone mixture as the extractant to produce a pure butadiene stream.

1 Claim, 1 Drawing Figure

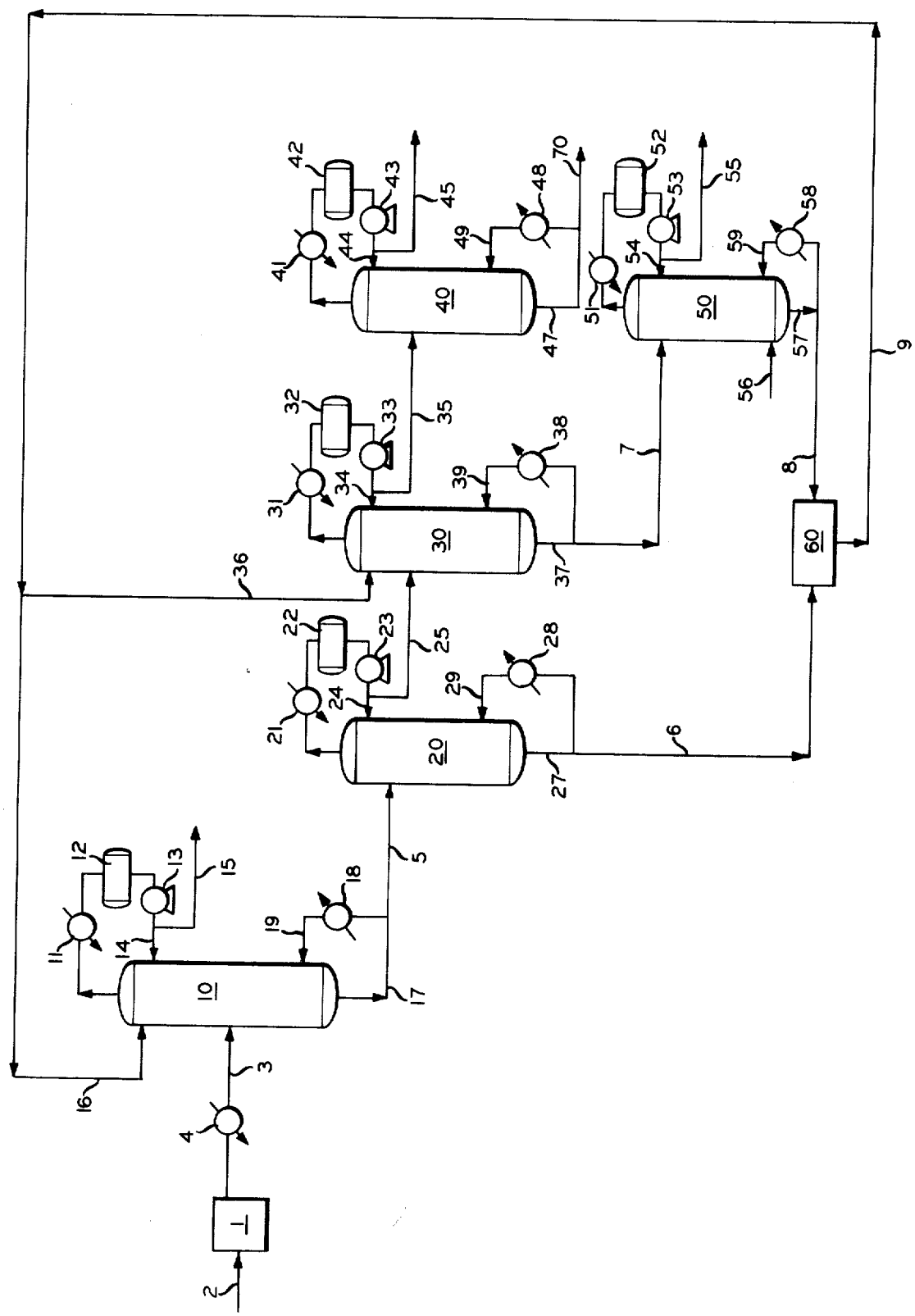

BUTADIENE PRODUCTION AND PURIFICATION

This invention relates to the purification of butadiene. In one of its more specific aspects, the invention relates to the removal of vinyl acetylene from a stream containing butadiene and vinyl acetylene. A further aspect of this invention relates to the production of butadiene.

BACKGROUND OF THE INVENTION

It is well known in the art that butadiene, an important monomer for the production of various polymers, can be produced by dehydrogenation of butane. During this process various byproducts are produced. These byproducts must be removed to produce butadiene that can be polymerized, e.g. into rubber polymers. One byproduct that has particular disadvantages is vinyl acetylene. This highly unsaturated compound is a poison for the catalysts that polymerize butadiene. Polymerization-grade butadiene, therefore, should contain less than 50 ppm, sometimes less than 10 ppm, vinyl acetylene.

THE INVENTION

One object of this invention thus is to provide a process for the purification of a butadiene-containing stream.

Another object of this invention consists in the removal of vinyl acetylene from a stream containing butadiene and vinyl acetylene.

A further object of this invention consists in the provision of a process for purifying a butadiene stream containing vinyl acetylene as a contaminant, the process being energy-conserving, simple and applicable to standard equipment.

These and other objects, embodiments, advantages and details of this invention will become apparent to those skilled in the art from the following description the invention, the examples, the appended claims and the drawing, which shows a schematic flow diagram of a separation and purification system for a butadiene plant.

In accordance with the invention, we have now found that an essentially pure, that is, vinyl acetylene-free, butadiene stream can be produced from a feedstream containing butadiene and vinyl acetylene by two extractive distillation steps and a butadiene fractionation step, utilizing for both extractive distillation steps an extractive solvent consisting of a mixture of sulfolane and acetone.

More specifically, we have now found that a butadiene-containing feedstream consisting essentially of butadiene, butylenes, n-butane, propylene, and vinyl acetylene can be effectively purified by introducing this feedstream into a separating zone comprising a first extractive distillation zone, extractively distilling said feedstream in said first extractive distillation zone with an extractant consisting essentially of a mixture of about 15 to 30 weight percent of acetone and about 85 to 70 weight percent of a sulfolane to produce an overhead stream comprising propylene, butylenes and n-butane, withdrawing from said separating zone a stream comprising butadiene and vinyl acetylene being essentially free of butylenes, n-butane and propylene, introducing said stream comprising butadiene and vinyl acetylene into a second extractive distillation zone, extractively distilling said stream comprising butadiene and vinyl acetylene with an extractant consisting essentially of a mixture of 15 to 30 weight percent of acetone and about 85 to 70 weight percent of a sulfolane, to produce an overhead stream consisting of butadiene free of vinyl acetylene and a bottoms stream comprising said extractant and vinyl acetylene, introducing said overhead stream of said second extractive distillation zone into a fractionation zone, fractionally distilling said overhead stream of said second extractive distillation zone in said fractionation zone to produce an overhead stream of essentially pure butadiene and recovering the stream of pure butadiene as the product of the process.

In accordance with one presently preferred embodiment, said separation zone in addition to said first extractive distillation zone comprises a first stripping zone. The bottoms stream of said first extractive distillation zone in this embodiment is introduced into said first stripping zone to produce a bottoms stream consisting essentially of said extractant and an overhead stream comprising butadiene and vinyl acetylene and being essentially free of butylenes, n-butane and propylene. This overhead stream is thereafter introduced into said second extractive distillation zone. The advantage of this embodiment resides in the fact that the total quantity of extractant being used in the first extractive distillation zone does not have to be carried all the way to the second extractive distillation zone. Only the stream comprising the butadiene and vinyl acetylene is being subjected to said second extractive distillation, which reduces both the energy necessary to carry out this separation step and the size of the equipment that has to be employed.

Furthermore, and in accordance with another embodiment of this invention, it is presently preferred to recover the extractant of said second extractive distillation zone by introducing the bottoms stream of said second distillation zone, which bottoms stream consists essentially of said extractant, vinyl acetylene and butadiene, into a second stripping zone to produce an overhead stream of vinyl acetylene diluted with butadiene and a bottom stream consisting essentially of said extractant. Since the vinyl acetylene is a rather dangerous compound, it is preferred to carry out this stripping step with a diluent which leaves said second stripping zone overhead together with the vinyl acetylene and thereby the risks involved in handling a concentrated vinyl acetylene stream. Examples of such diluents are fuel gas, flue gas or inert gases. Such diluent gases are preferably injected in the bottom of the stripping zone to insure that that vinyl acetylene is adequately diluted throughout the zone. The presently preferred diluent is fuel gas.

Advantageously and in accordance with a still further embodiment of this invention, the extractant from the bottoms stream of said first stripping zone and the extractant from the bottoms stream of said second stripping zone may be combined for purposes of heat exchange and handling and recycled into the first and second extractive distillation zones as the extractant.

Since in most cases the feedstream to be purified contains butylenes, a major portion of the butylenes in accordance with a preferred embodiment of this invention is withdrawn via the overhead stream for said first extractive distillation zone whereas a minor portion of these butylenes is withdrawn via the bottoms stream withdrawn from the first fractionation zone.

In accordance with another embodiment of this invention, there is provided a process for the production of butadiene. This process comprises the steps of introducing at least one $C_4$-hydrocarbon selected from the group consisting of n-butane, 1-butylene and 2-butylene into a dehydrogenation zone. At least a portion of these C$_4$-hydrocarbons is dehydrogenated in this dehydrogenation zone to produce a reactor effluent containing butadiene, butylenes, C$_4$ feed, propylene and vinyl acetylene. This reactor effluent is then introduced into the first extractive distillation zone of said separation zone and treated as described above in connection with the separating or purifying method.

The presently preferred process to produce butadiene comprises introducing butenes into the dehydrogenation zone and contacting these butenes in this dehydrogenation zone under oxidative dehydrogenation conditions with a dehydrogenation catalyst consisting essentially of phosphorus, tin and a Group IA or Group IIA metal compound.

Advantageously and preferably, the butylenes produced during the separation steps, e.g., as part of the overhead stream of the first extractive distillation zone and as part of the bottoms stream of the fractionation zone, are reintroduced into the dehydrogenation zone.

The extractant used in the two extractive distillation zones consists preferably of 15 to 30 weight percent acetone and 85 to 70 weight percent of a sulfolane. The most preferred composition of the extractant is about 25 weight percent of acetone mixed with about 75 weight percent of a sulfolane.

The sulfolane which can be used in accordance with this invention as a portion of the extractant for the two extractive distillation zones is defined by the formula

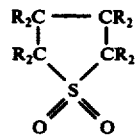

in which the radicals R, which can be the same or different, are individually selected from the group of radicals consisting of hydrogen, alkyl, cycloalkyl, and aryl radicals which in turn can be unsubstituted or substituted by alkyl, cycloalkyl and aryl radicals. The hydrocarbyl radicals R contain up to 10 carbon atoms each. The total number of carbon atoms in the sulfolane is 4 to 14. Examples for sulfolanes useful in accordance with this invention are unsubstituted sulfolane and 2-methyl-, 3-methyl-, 2-ethyl-, 2,5-dimethyl-, 2,4-dimethyl-, 2,3-dimethyl-, 3,4-dimethyl, 2,2-dimethyl-, 3-ethyl, 2-propyl-, 2-methy-5-ethyl-, 2-isopropyl-, 2,3,5-trimethyl-, 2,2,4-trimethyl-, 2-hexyl-, 2,3-dimethyl-5-butyl-, 2-cyclohexyl-, 2-cyclohexyl-4-methyl-, 2-phenyl-, 3-phenyl-, and 2-phenyl-5-ethylsulfolanes. The presently preferred sulfolanes are an unsubstituted sulfolane (all eight radicals R in the above-shown formula are H) and 3-methylsulfolane.

The operating conditions of the individual steps of this invention are not overly critical and depend to a large extent upon the composition of the feedstreams. The usually employed and the preferred ranges for the operating conditions of the various steps are shown in the following table:

TABLE I

|  | Usually employed range | Preferred range |  | Metric System Usually employed range | Preferred range |
| --- | --- | --- | --- | --- | --- |
| First extractive distillation zone: |  |  |  |  |  |
| pressure, psig | 65–100 | 70–90 | MPa | 0.45–0.69 | 0.48–0.62 |
| bottom temp., °F | 200–260 | 205–250 | °C. | 93–127 | 96–121 |
| overhead temp., °F. | 117–135 | 120–130 | °C. | 47–57 | 49–54 |
| number of trays | 100–200 | 150–200 | — | — | — |
| First stripping zone: |  |  |  |  |  |
| pressure, psig | 50–85 | 60–75 | MPa | 0.34–0.59 | 0.41–0.52 |
| bottom temp., °F. | 270–310 | 280–300 | °C. | 132–154 | 138–149 |
| overhead temp., °F. | 107–135 | 116–129 | °C. | 42–57 | 47–54 |
| number of trays | 10–50 | 20–40 | — | — | — |
| Second extractive distillation zone: |  |  |  |  |  |
| pressure, psig | 55–77 | 64–71 | MPa | 0.38–0.53 | 0.44–0.49 |
| bottom temp., °F. | 259–300 | 259–285 | °C. | 126–149 | 126–140 |
| overhead temp., °F. | 110–130 | 120–125 | °C. | 43–54 | 49–52 |
| number of trays | 20–50 | 30–50 | — | — | — |
| Fractionation zone: |  |  |  |  |  |
| pressure, psig | 50–85 | 60–75 | MPa | 0.34–0.59 | 0.41–0.52 |
| bottom temp., °F. | 125–160 | 130–155 | °C. | 52–71 | 54–68 |
| overhead temp., °F. | 107–135 | 116–129 | °C. | 42–57 | 47–54 |
| number of trays | 100–200 | 100–150 |  |  |  |
| Second stripping zone: |  |  |  |  |  |
| pressure, psig | 52–58 | 52–58 | MPa | 0.36–0.40 | 0.36–0.40 |
| bottom temp., °F. | 290–310 | 295–310 | °C. | 143–154 | 146–154 |
| overhead temp., °F. | 109–120 | 110–120 | °C. | 43–49 | 43–49 |
| number of trays | 20–40 | 20–30 | — | — | — |

In the embodiment of this invention relating to the production of butadiene, the dehydrogenation steps are known in the art. The present invention in the embodiment consists in the combination of the dehydrogenation steps with the specific purification steps. Both a two-step dehydrogenation in which butane in the first step is dehydrogenated to butene and butene in the second step is dehydrogenated to butadiene and a one-step process in which butane is directly dehydrogenated to butadiene are encompassed by the scope of this invention. Details concerning the two-sep dehydrogenation to produce butadiene are shown, e.g., in the U.S. Patent Nos. 2,362,218, 2,367,622, 2,376,323, 2,381,692 and 2,386,310. The one-step process for dehydrogenating butane directly to butadiene, or the oxidative dehydrogenation process, is shown in detail, e.g., in the U.S. Pat. Nos. 2,371,809 and 2,376,061.

The invention will be still more fully understood from the following description of the schematic flow diagram shown in the drawing.

Into a dehydrogenation section 1 a C$_4$-hydrocarbon feedstream is introduced via line 2. This dehydrogenation section 1 can be, as explained, either a two-stage dehydrogenation section or a one-stage dehydrogenation section. The reactor effluent from the reactor 1 is withdrawn and passed through a gas plant (not shown) and thereafter via conduit 3 and a cooler 4 and is fed into a first extractive distillation zone 10. From this first extractive distillation zone 10 an overhead stream is passed through a condenser 11, a liquid knockout vessel 12 and a pump 13. Part of the overhead stream is withdrawn via line 15 and part of the overhead stream is reintroduced into the extractive distillation zone 10 via line 14 as a reflux stream. This overhead stream from the extractive distillation zone 10 contains all the propylene, all the methyl acetylene, all the n-butane, essentially all the butene-1 and the transbutene-2 contained in the feedstream 3 entering the first extractive distillation zone 10. A small quantity of butadiene also leaves overhead from the first extractive distillation zone 10. This quantity is less than about 0.1 percent of the total butadiene contained in the feedstream 3.

Via line 16 an extractant consisting essentially of acetone and sulfolane is introduced into the first extractive distillation zone. From the bottom of the first extractive distillation zone 10 a liquid bottoms stream is removed via line 17. Part of the liquid bottoms stream is heated in a reboiler 18 and fed back into the lower portion of the first extractive distillation zone 10 via line 19, and the remainder passes via line 5 to a first stripping zone 20. An overhead stream withdrawn from the first stripping zone 20 is condensed in condenser 21 and passed through a liquid knockout vessel 22 into pump 23. This overhead stream is partially reintroduced as reflux via line 24 into the upper portion of the first stripping zone 20. The remainder of the overhead stream is passed on via line 25 into a second extractive distillation zone 30.

From the bottom of the first stripping zone 20 a liquid bottoms stream is withdrawn via line 27. A portion of this liquid bottoms stream is heated in a reboiler 28 and fed into the lower portion of the first stripping zone 20 via line 29.

The remainder of the bottoms stream of line 27 is passed via line 6 to a collecting unit 60 which may comprise additional cooling and cleaning devices for the arriving streams.

The liquid bottoms stream of the first stripper 20 consists essentially of the extractive solvent alone. The gaseous overhead of the first stripping zone 20 consists of butadiene, vinyl acetylene and some butenes.

Part of the stream leaving the first stripping zone overhead is introduced via line 25 into the second extractive distillation zone 30. An essentially gaseous stream leaves the second extractive distillation zone overhead, is passed via condenser 31 and a liquid knockout vessel 32 to a pump 33. A portion of this overhead stream is reintroduced into the second extractive distillation zone via line 34 as reflux and another portion of this overhead stream is passed via line 35 to a fractionator 40.

An extractive solvent consisting essentially of 25 weight percent acetone and 75 weight unsubstituted sulfolane is passed via line 36 into said second extractive distillation zone. This extractant mixture acts as a selective solvent for the vinyl acetylene in the butadiene/vinyl acetylene mixture.

A liquid bottoms stream is withdrawn from the second extractive distillation zone 30 via a line 37. Part of this liquid bottoms stream is reheated in a reboiler 38 and reintroduced into the lower section of the second extractive distillation zone 30 via line 39. The remainder of the liquid bottoms stream in line 37 is passed via line 7 to a second stripping zone 50. An overhead stream from the second stripping zone 50 is passed through a condenser 51 and a knockout vessel 52 to a pump 53. Part of this overhead stream is reintroduced via line 54 into the upper portion of the second stripping zone 50 whereas the rest of the overhead stream is recovered via line 55.

Via line 56 a stream of fuel gas is introduced near the bottom of the second stripping zone 50. This fuel gas serves to dilute the vinyl acetylene concentration in order to avoid any explosion hazards.

A liquid bottoms stream leaves the second stripping zone 50 via line 57. A portion of this bottoms stream is heated in the reboiler 58 and reintroduced via line 59 into the lower portion of the second stripping zone 50. The remainder of the liquid bottoms stream 57 is passed via line 8 to the collecting unit 60.

From the collecting unit 60 a stream of extractant is withdrawn via line 9. This stream of extractant in line 9 is split up betweem the two streams 16 and 36 entering the two extractive distillation zones 10 and 30.

The overhead stream 35 from the second extractive distillation zone 30 and consisting essentially of butadiene and butene-2 is introduced into a fractionator 40. From this fractionator 40 an overhead stream is passed via condenser 41 and knockout vessel 42 to a pump 43. A portion of this overhead stream is reintroduced into the upper section of the fractionator 40 via line 44. The remainder of the overhead stream is recovered via line 45. The overhead stream 45 consists essentially of butadiene together with trace quantities of butenes.

From the bottom of the fractionator 40 a liquid stream is removed via line 47. Part of this liquid stream 47 is reheated in a reboiler 48 and reintroduced into the lower portion of the fractionator 40 via line 49. The remainder of the liquid bottoms stream 47 is recovered via line 70. This bottoms stream recovered via line 70 consists essentially of cis-butene-2, as well as some butadiene.

The invention will be still more fully understood from the following example. This example is based on actual runs carried out with the individual stages of separation 10, 20, 30 and 40. The results of these individual runs have been used to calculate a material balance for the overall process.

EXAMPLE

Into a separating unit as shown in the drawing a feedstream consisting essentially of propylene, butene-1, butadiene, n-butane, cis- and trans- butene-2, methyl acetylene and vinyl acetylene is introduced via line 3. An extractive solvent consisting of 25 weight percent of acetone and 75 weight percent of unsubstituted sulfolane is used in the extractant feedstreams to the first extractive distillation zone 10 and the second extractive distillation zone 30. 473,200 Pounds per hour extractive solvent are introduced via line 16 into the first extractive distillation zone 10 and 121,000 pounds of extractant per hour are introduced via line 36 into the second extractive distillation zone 30. The results of the various distillation and fractionation steps as far as they are relevant to the present invention are shown in the following table:

TABLE II

| | (Units: lbs/hr) | | | | | | | |
|---|---|---|---|---|---|---|---|---|
| Stream number | Feed-stream | Overhead, butadiene absorber | Stripper feed | Butadiene fractionator feed | Bottoms, vinyl acetylene absorber | Vinyl acetylene reject | Butadiene product | Butadiene fractionator bottoms |
| in drawing | 3 | 15 | 5 | 35 | 7 | 55 | 45 | 70 |
| Components: | | | | | | | | |
| Propylene | 364 | 364 | — | — | — | — | — | — |
| Butene-1 | 11,648 | 11,540 | 108 | 108 | — | — | 108 | — |
| Butadiene | 45,136 | 40 | 45,096 | 44,609 | 487 | 487 | 44,133 | 476 |
| n-Butane | 4,732 | 4,732 | — | — | — | — | — | — |
| cis- and trans-Butene-2 | 10,920 | 9,736 | 1,184 | 1,184 | — | — | 100 | 1,084 |
| Methyl acetylene | 11 | 11 | — | — | — | — | — | — |
| Vinyl acetylene | 162 | — | 162 | — | 162 | 162 | — | — |
| Extractive solvent | — | — | 473,200 | — | 121,000 | — | — | — |
| Totals | 72,973 | 26,423 | 519,750 | 45,901 | 121,649 | 649 | 44,341 | 1,560 |

As can be seen from the results in the above-shown Table II, the process of this invention provides an effective separation of vinyl acetylene from a C$_4$- concentrate. A purified butadiene stream is produced containing less than ½ percent of butene impurities.

Reasonable variations and modifications which will be apparent to those skilled in the art can be made in this invention without departing from the spirit and scope thereof.

We claim:

1. A process for producing a polymerization grade butadiene stream comprising a. dehydrogenating a C$_4$-hydrocarbon stream containing at least one of the members selected from the group consisting of butane and butylenes in the presence of a dehydrogenation catalyst consisting essentially of phosphorus, tin, and a Group Ia or IIa metal compound under dehydrogenation conditions to produce a dehydrogenation effluent stream, b. separating from this dehydrogenation effluent stream a feed stream consisting essentially of butadiene, butylenes, n-butane, propylene and vinylacetylene, c. extractively distilling said feed stream utilizing as an extractant a mixture of about 15 to 30 weight percent of acetone and about 85 to 70 weight percent of a sulfolane having the formula

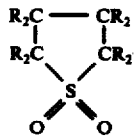

wherein the radicals R, which can be the same or different, are individually selected from the group consisting of hydrogen, alkyl, cycloalkyl, aryl, which radicals in turn can be unsubstituted or substituted by alkyl, cycloalkyl, and aryl radicals, each hydrocarbyl radical R having up to 10 carbon atoms and the sulfolane having 4 to 14 carbon atoms per molecule, to produce a first overhead stream consisting essentially of propylene, n-butane and butylenes, and a first bottom stream consisting essentially of butadiene, vinylacetylene, butylenes and said extractant, d. stripping said first bottom stream to produce a first stripper bottom stream consisting essentially of said extractant and a first stripper overhead stream consisting essentially of butadiene, butylenes and vinylacetylene and being essentially free of said extractant, e. extractively distilling said first stripper overhead stream utilizing the same extractant as defined in step c to form a second bottom stream consisting essentially of said extractant, butadiene, and vinylacetylene and a second overhead stream consisting essentially of butadiene and butylenes, f. fractionating said second stripper overhead stream to produce a third overhead stream consisting essentially of said polymerization grade butadiene as the product of the process, and a third bottom stream consisting essentially of butylenes and some butadiene, g. stripping said second bottom stream to form a second stripper bottom stream consisting essentially of said extractant and a second stripper overhead stream, h. combining said first and said second stripper bottom stream to form one extractant stream, i. recycling a first portion of said extractant stream as said extractant in step (c), j. recycling a second portion of said extractant stream as said extractant in step (e), and k. recycling said first overhead stream and said third bottom stream to step a as part of the C$_4$-hydrocarbon feed.

* * * * *